US006399852B1

(12) United States Patent
Barron

(10) Patent No.: US 6,399,852 B1
(45) Date of Patent: Jun. 4, 2002

(54) BANDAGE ASSEMBLY

(76) Inventor: Gary Barron, 1221 Witter, Pasadena, TX (US) 77506

( * ) Notice: Subject to any disclaimer, the term of this patent is extended or adjusted under 35 U.S.C. 154(b) by 0 days.

(21) Appl. No.: 09/780,008

(22) Filed: Feb. 9, 2001

(51) Int. Cl.$^7$ ................................................. A61F 13/00
(52) U.S. Cl. ........................................... 602/41; 602/79
(58) Field of Search .............................. 602/41, 42, 63, 602/74, 75, 78, 79; D24/189; 2/170; 604/308; 606/201; 128/876–879

(56) References Cited

U.S. PATENT DOCUMENTS

| | | | | |
|---|---|---|---|---|
| 3,245,406 A | * | 4/1966 | Chardack | 602/79 |
| 3,724,457 A | * | 4/1973 | Klatte | 602/79 |
| 3,779,242 A | * | 12/1973 | McCullough | 602/79 |
| 4,926,848 A | | 5/1990 | Shimkus et al. | |
| D341,424 S | | 11/1993 | Lurie | |
| 5,267,952 A | | 12/1993 | Gardner | |
| 5,445,601 A | * | 8/1995 | Harlow | 602/19 |
| 5,456,660 A | * | 10/1995 | Reich et al. | 602/79 |
| 5,624,391 A | | 4/1997 | Fan et al. | |
| 5,807,300 A | * | 9/1998 | Nix, Jr. | 602/79 |
| 5,823,977 A | * | 10/1998 | Dalyea | 602/3 |
| 5,843,025 A | * | 12/1998 | Shaari | 602/53 |
| 5,876,365 A | | 3/1999 | Hart | |
| 5,897,519 A | * | 4/1999 | Shesol et al. | 602/79 |
| 5,921,949 A | * | 7/1999 | Dray | 602/64 |
| 6,258,051 B1 | * | 7/2001 | Shesol et al. | 602/79 |

* cited by examiner

Primary Examiner—Kim M. Lewis

(57) ABSTRACT

A bandage assembly for providing a non-stick repositionable wound dressing. The bandage assembly includes a bandage member with a pad portion on the first face and a first portion of hook and loop fastener on a second face, a backing member with a first face having a complementary second portion of hook and loop fastener and a second face having a third portion of hook and loop fastener, and a band member with opposite ends, each of the opposite ends having a fourth and fifth portion of hook and loop fastener respectively, both the fourth and fifth portions being complementary to the third portion.

10 Claims, 2 Drawing Sheets

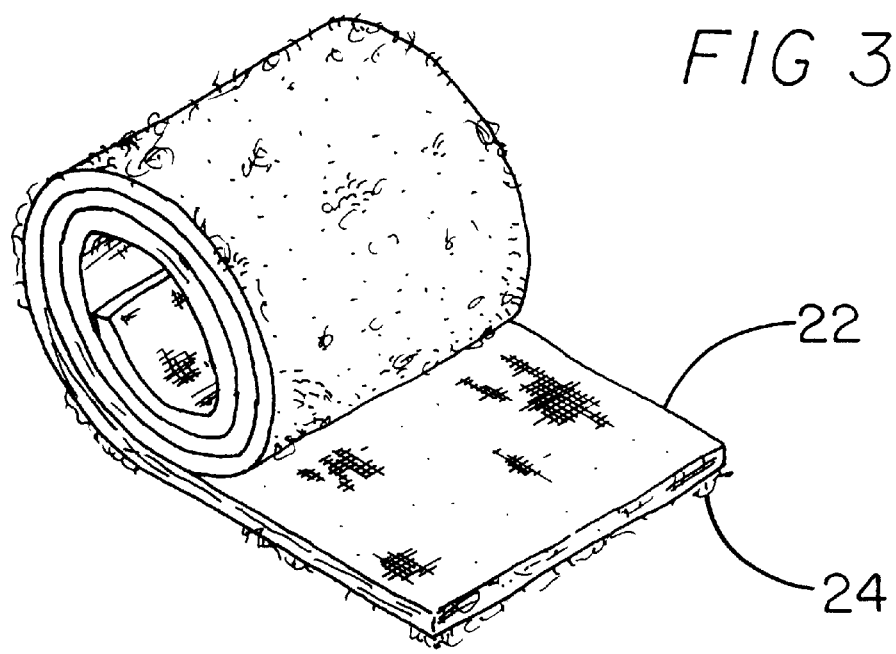
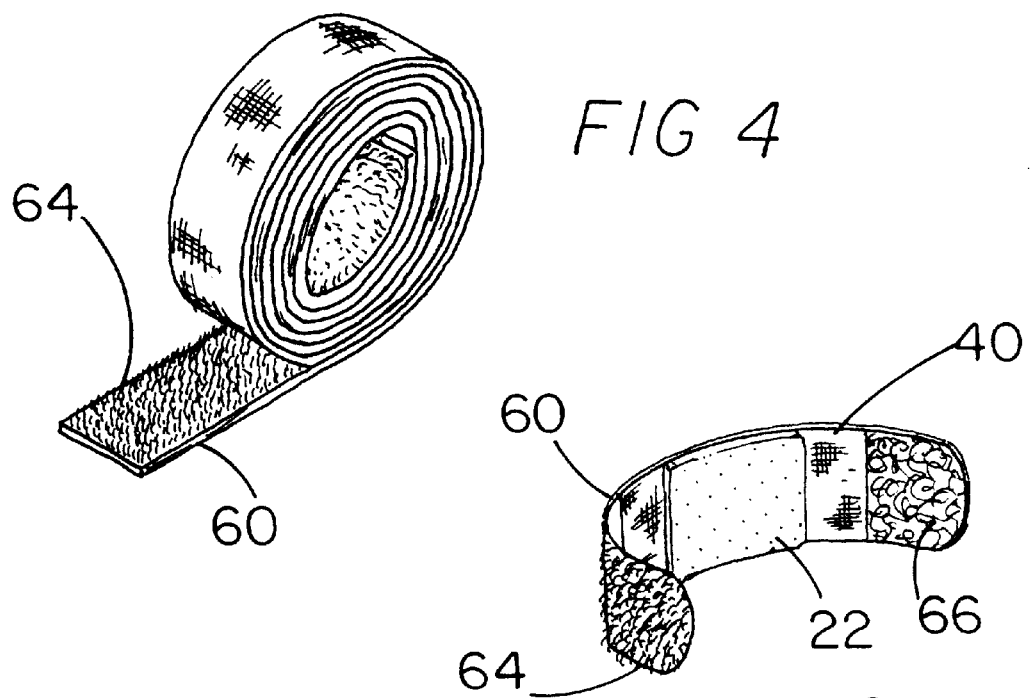

BANDAGE ASSEMBLY

BACKGROUND OF THE INVENTION

1. Field of the Invention

The present invention relates to wound dressings and more particularly pertains to a new bandage assembly for providing a non-stick repositionable wound dressing.

2. Description of the Prior Art

The use of wound dressings is known in the prior art. More specifically, wound dressings heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,456,660; U.S. Pat. No. 5,876,365; U.S. Pat. No. 5,624,391; U.S. Pat. No. 5,267,952; U.S. Pat. No. 4,926,848; and U.S. Pat. No. Des. 341,424.

While these devices fulfill their respective, particular objectives and requirements, the aforementioned patents do not disclose a new bandage assembly. The inventive device includes a bandage member with a pad portion on the first face and a first portion of hook and loop fastener on a second face, a backing member with a first face having a complementary second portion of hook and loop fastener and a second face having a third portion of hook and loop fastener, and a band member with opposite ends, each of the opposite ends having a fourth and fifth portion of hook and loop fastener respectively, both the fourth and fifth portions being complementary to the third portion.

In these respects, the bandage assembly according to the present invention substantially departs from the conventional concepts and designs of the prior art, and in so doing provides an apparatus primarily developed for the purpose of providing a nonstick repositionable wound dressing.

SUMMARY OF THE INVENTION

In view of the foregoing disadvantages inherent in the known types of wound dressings now present in the prior art, the present invention provides a new bandage assembly construction wherein the same can be utilized for providing a non-stick repositionable wound dressing.

The general purpose of the present invention, which will be described subsequently in greater detail, is to provide a new bandage assembly apparatus and method which has many of the advantages of the wound dressings mentioned heretofore and many novel features that result in a new bandage assembly which is not anticipated, rendered obvious, suggested, or even implied by any of the prior art wound dressings, either alone or in any combination thereof.

To attain this, the present invention generally comprises a bandage member with a pad portion on the first face and a first portion of hook and loop fastener on a second face, a backing member with a first face having a complementary second portion of hook and loop fastener and a second face having a third portion of hook and loop fastener, and a band member with opposite ends, each of the opposite ends having a fourth and fifth portion of hook and loop fastener respectively, both the fourth and fifth portions being complementary to the third portion.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new bandage assembly apparatus and method which has many of the advantages of the wound dressings mentioned heretofore and many novel features that result in a new bandage assembly which is not anticipated, rendered obvious, suggested, or even implied by any of the prior art wound dressings, either alone or in any combination thereof.

It is another object of the present invention to provide a new bandage assembly which may be easily and efficiently manufactured and marketed.

It is a further object of the present invention to provide a new bandage assembly which is of a durable and reliable construction.

An even further object of the present invention is to provide a new bandage assembly which is susceptible of a low cost of manufacture with regard to both materials and labor, and which accordingly is then susceptible of low prices of sale to the consuming public, thereby making such bandage assembly economically available to the buying public.

Still yet another object of the present invention is to provide a new bandage assembly which provides in the apparatuses and methods of the prior art some of the advantages thereof, while simultaneously overcoming some of the disadvantages normally associated therewith.

Still another object of the present invention is to provide a new bandage assembly for providing a non-stick repositionable wound dressing.

Yet another object of the present invention is to provide a new bandage assembly which includes a bandage member with a pad portion on the first face and a first portion of hook and loop fastener on a second face, a backing member with a first face having a complementary second portion of hook and loop fastener and a second face having a third portion of hook and loop fastener, and a band member with opposite ends, each of the opposite ends having a fourth and fifth portion of hook and loop fastener respectively, both the fourth and fifth portions being complementary to the third portion.

Still yet another object of the present invention is to provide a new bandage assembly that is non-adhesive.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a schematic perspective view of the bandage member of an embodiment of the present invention.

FIG. 4 is a schematic perspective view of the band member of an embodiment of the present invention.

FIG. 5 is a schematic perspective view of and embodiment of the present invention.

DESCRIPTION OF THE PREFERRED EMBODIMENT

Figure 1:
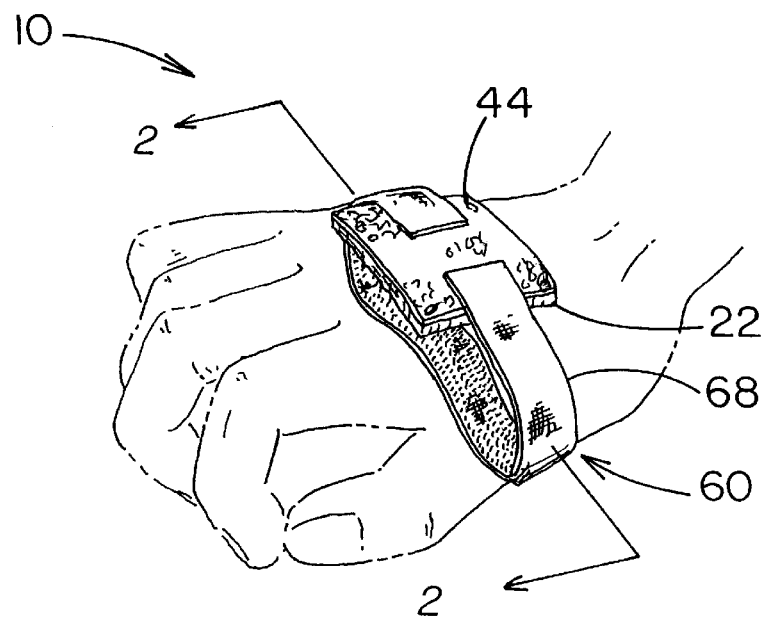
FIG. 1 is a schematic perspective view of a new bandage assembly according to the present invention.
Figure 2:
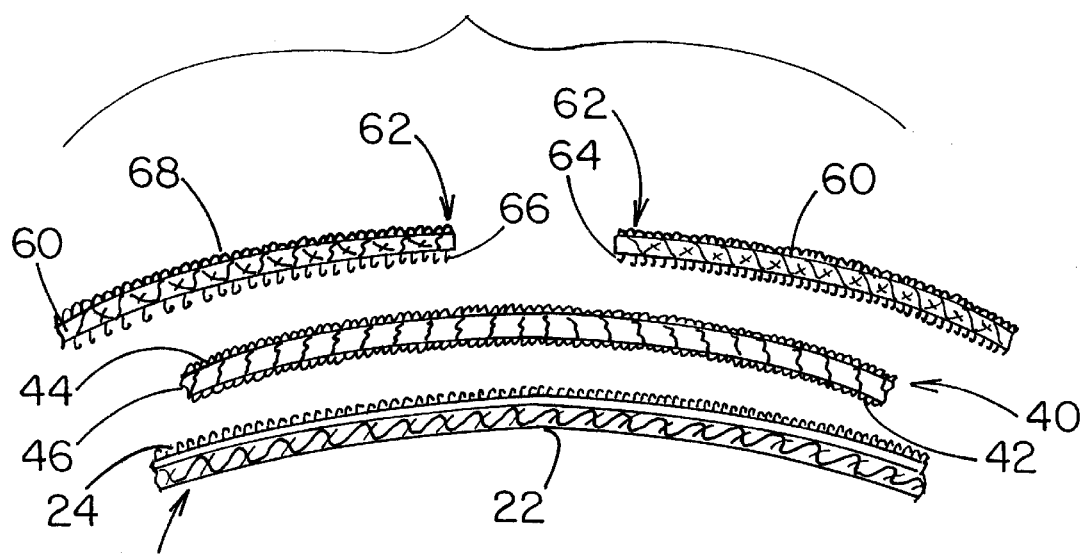
FIG. 2 is a schematic exploded cross-sectional view of the present invention taken along line 2—2 of FIG. 1.

With reference now to the drawings, and in particular to FIGS. 1 through 5 thereof, a new bandage assembly embodying the principles and concepts of the present invention and generally designated by the reference numeral 10 will be described.

As best illustrated in FIGS. 1 through 5, the bandage assembly 10 generally comprises a bandage member 20, a backing member 40, and a band member 60.

The bandage member 20 includes a pad portion 22 on a first face of the bandage member 20. The bandage member 20 includes a first portion of hook and loop fastener 24 on a second face of the bandage member 20.

In an embodiment the bandage member 20 comprises stretchable elastic and the pad portion 22 comprises gauze.

The backing member 40 includes a second portion of hook and loop fastener 42 covering a first face of the backing member 20. The second portion of hook and loop fastener 42 is complimentary to the first portion of hook and loop fastener 24. Thus the second portion of hook and loop fastener 42 is selectively engageable to the first portion of hook and loop fastener 24.

The backing member 40 includes a second face opposite the first face of the backing member 40. The second face of the backing member 40 is covered by third portion of hook and loop fastener 44.

The band member 60 includes opposite ends 62. Each of the opposite ends 62 includes a respective fourth 64 and fifth portion of hook and loop fastener 66. The fourth 64 and fifth portions of hook and loop fastener 66 are complimentary to the third portion of hook and loop fastener 44 such that the opposite ends 62 of the band member 60 are selectively engageable to the third portion of hook and loop fastener 44. Thus the band 60 is designed for positioning around a user for holding the bandage member 20 against the user.

The backing member 40 includes a flexible core portion 46 positioned between the second 42 and third portions of the hook and loop fastener 44.

The second 42 and third portions of hook and loop fastener 44 are integrally joined such that the second 42 and third portions of hook and loop fastener 44 envelope the core portion 46 of the backing member 40.

The first portion of hook and loop fastener 24 covers an entirety of the second face of the bandage member 20 for facilitating engagement of the backing member 40 to the second face.

The band member 60 includes an elastic medial portion for facilitating firm holding of the bandage member 20 against the user.

The fourth 64 and fifth portions of hook and loop fastener 66 are integrally joined to cover an entirety of a first face of the band member 60 such that the band member 60 is designed for wrapping multiple times around the user to facilitate securement of the bandage member 20 against the user.

A sixth portion of hook and loop fastener 68 is positioned on a second face of the band member 60. The sixth portion of hook and loop fastener 68 is complimentary to the fourth 64 and fifth portions of hook and loop fastener 66 such that the first face of the band member 60 is selectively engageable to the second face of the band member 60 for facilitating securement of the band member 60 around the user.

The bandage member 20 is cuttable such that the bandage member 20 is designed for facilitating shaping of a perimeter edge of the bandage member 20 for covering a wound.

In an embodiment, the portions of hook and loop fastener are deployed differently. The backing member 40 includes a backing member portion of hook and loop fastener 42 covering a first face of the backing member 40. The backing member portion of hook and loop fastener 42 is complimentary to the bandage portion of hook and loop fastener 24. Thus the backing member portion of hook and loop fastener 42 is selectively engageable to the bandage portion of hook and loop fastener 24. The backing member 40 includes a second face opposite the first face of the backing member 40. The second face of the backing member is covered by the backing member portion of hook and loop fastener 42. The band member 60 includes opposite ends 62. A first band end portion of hook and loop fastener 64 is coupled to a first face of the band member 60 adjacent one of the opposite ends 62. The first band end portion of hook and loop fastener 64 is complimentary to the backing member portion of hook and loop fastener 42 such that the one of the opposite ends 62 of the band member 60 are selectively engageable to the backing member portion of hook and loop fastener 42. A second band end portion of hook and loop fastener 66 is positioned on a second face of the band member 60 adjacent to another of the opposite ends 62. The second band end portion of hook and loop fastener 66 is complimentary to the first end portion of hook and loop fastener 64 such that the one of the opposite ends 62 of the band member 60 is selectively engageable to the other of the opposite ends 62 of the band member 60. Thus the band 60 is designed for positioning around a user for holding the bandage member 20 against the user.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A bandage assembly comprising:
   a bandage member having a pad portion on a first face of said bandage member, said bandage member having a first portion of hook and loop fastener on a second face of said bandage member;
   a backing member, said backing member having a second portion of hook and loop fastener covering a first face of said backing member, said second portion of hook and loop fastener being complimentary to said first portion of hook and loop fastener whereby said second portion of hook and loop fastener is selectively engageable to said first portion of hook and loop fastener;
   said backing member having a second face opposite said first face of said backing member, said second face of said backing member being covered by third portion of hook and loop fastener;
   a band member, said band member having opposite ends, each of said opposite ends having a respective fourth and fifth portion of hook and loop fastener, said fourth and fifth portions of hook and loop fastener being complimentary to said third portion of hook and loop fastener such that said opposite ends of said band member are selectively engageable to said third portion of hook and loop fastener whereby said band is adapted for positioning around a user for holding said bandage member against the user.

2. The bandage assembly of claim 1, further comprising:
   said backing member having a flexible core portion positioned between said second and third portions of said hook and loop fastener.

3. The bandage assembly of claim 2, further comprising:
   said second and third portions of hook and loop fastener being integrally joined such that said second and third portions of hook and loop fastener envelope said core portion of said backing member.

4. The bandage assembly of claim 1, further comprising:
   said first portion of hook and loop fastener covering an entirety of said second face of said bandage member for facilitating engagement of said backing member to said second face.

5. The bandage assembly of claim 1, further comprising:
   said band member having an elastic medial portion for facilitating firm holding of said bandage member against the user.

6. The bandage assembly of claim 1, further comprising:
   said fourth and fifth portions of hook and loop fastener being integrally joined to cover an entirety of a first face of said band member such that said band member is adapted for wrapping multiple times around the user to facilitate securement of the bandage member against the user.

7. The bandage assembly of claim 6, further comprising:
   a sixth portion of hook and loop fastener positioned on a second face of said band member, said sixth portion of hook and loop fastener being complimentary to said fourth and fifth portions of hook and loop fastener such that said first face of said band member is selectively engageable to said second face of said band member for facilitating securement of said band member around the user.

8. The bandage assembly of claim 1, further comprising:
   said bandage member being cuttable such that said bandage member is adapted for facilitating shaping of a perimeter edge of said bandage member for covering a wound.

9. A bandage assembly comprising:
   a bandage member having a pad portion on a first face of said bandage member, said bandage member having a first portion of hook and loop fastener on a second face of said bandage member;
   a backing member, said backing member having a second portion of hook and loop fastener covering a first face of said backing member, said second portion of hook and loop fastener being complimentary to said first portion of hook and loop fastener whereby said second portion of hook and loop fastener is selectively engageable to said first portion of hook and loop fastener;
   said backing member having a second face opposite said first face of said backing member, said second face of said backing member being covered by third portion of hook and loop fastener;
   a band member, said band member having opposite ends, each of said opposite ends having a respective fourth and fifth portion of hook and loop fastener, said fourth and fifth portions of hook and loop fastener being complimentary to said third portion of hook and loop fastener such that said opposite ends of said band member are selectively engageable to said third portion of hook and loop fastener whereby said band is adapted for positioning around a user for holding said bandage member against the user;
   said backing member having a flexible core portion positioned between said second and third portions of said hook and loop fastener;
   said second and third portions of hook and loop fastener being integrally joined such that said second and third portions of hook and loop fastener envelope said core portion of said backing member;
   said first portion of hook and loop fastener covering an entirety of said second face of said bandage member for facilitating engagement of said backing member to said second face;
   said band member having an elastic medial portion for facilitating firm holding of said bandage member against the user;
   said fourth and fifth portions of hook and loop fastener being. integrally joined to cover an entirety of a first face of said band member such that said band member is adapted for wrapping multiple times around the user to facilitate securement of the bandage member against the user;

a sixth portion of hook and loop fastener positioned on a second face of said band member, said sixth portion of hook and loop fastener being complimentary to said fourth and fifth portions of hook and loop fastener such that said first face of said band member is selectively engageable to said second face of said band member for facilitating securement of said band member around the user; and said bandage member being cuttable such that said bandage member is adapted for facilitating shaping of a perimeter edge of said bandage member for covering a wound.

10. A bandage assembly comprising:

a bandage member having a pad portion on a first face of said bandage member, said bandage member having a bandage portion of hook and loop fastener on a second face of said bandage member;

a backing member, said backing member having a backing member portion of hook and loop fastener covering a first face of said backing member, said backing member portion of hook and loop fastener being complimentary to said bandage portion of hook and loop fastener whereby said backing member portion of hook and loop fastener is selectively engageable to said bandage portion of hook and loop fastener;

said backing member having a second face opposite said first face of said backing member, said second face of said backing member being covered by said backing member portion of hook and loop fastener;

a band member, said band member having opposite ends, a first band end portion of hook and loop fastener coupled to a first face of said band member adjacent one of said opposite ends, said first band end portion of hook and loop fastener being complimentary to said backing member portion of hook and loop fastener such that said one of said opposite ends of said band member is selectively engageable to said backing member portion of hook and loop fastener;

a second band end portion of hook and loop fastener positioned on a second face of said band member adjacent to another of said opposite ends, said second band end portion of hook and loop fastener being complimentary to said first end portion of hook and loop fastener such that said one of said opposite ends of said band member is selectively engageable to said other of said opposite ends of said band member whereby said band is adapted for positioning around a user for holding said bandage member against the user;

said backing member having a flexible core portion;

said bandage portion of hook and loop fastener covering an entirety of said second face of said bandage member for facilitating engagement of said backing member to said second face;

said band member having an elastic medial portion for facilitating firm holding of said bandage member against the user; and said bandage member being cuttable such that said bandage member is adapted for facilitating shaping of a perimeter edge of said bandage member for covering a wound.

* * * * *